(12) United States Patent
Abe

(10) Patent No.: US 11,651,616 B2
(45) Date of Patent: May 16, 2023

(54) DETECTION DEVICE

(71) Applicant: Japan Display Inc., Tokyo (JP)

(72) Inventor: Hiroyuki Abe, Tokyo (JP)

(73) Assignee: Japan Display Inc., Tokyo (JP)

( * ) Notice: Subject to any disclaimer, the term of this patent is extended or adjusted under 35 U.S.C. 154(b) by 179 days.

(21) Appl. No.: 17/165,482

(22) Filed: Feb. 2, 2021

(65) Prior Publication Data

US 2021/0240962 A1   Aug. 5, 2021

(30) Foreign Application Priority Data

Feb. 3, 2020  (JP) .............................. JP2020-016529

(51) Int. Cl.

| | |
|---|---|
| *H01L 31/072* | (2012.01) |
| *G06V 40/13* | (2022.01) |
| *H01L 27/146* | (2006.01) |
| *G06V 40/12* | (2022.01) |
| *H01L 27/28* | (2006.01) |
| *A61B 5/1172* | (2016.01) |
| *A61B 5/024* | (2006.01) |

(52) U.S. Cl.
CPC ...... *G06V 40/1318* (2022.01); *G06V 40/1394* (2022.01); *H01L 27/14636* (2013.01); *H01L 27/14643* (2013.01); *H01L 27/14678* (2013.01); *H01L 27/288* (2013.01); *A61B 5/02416* (2013.01); *A61B 5/1172* (2013.01)

(58) Field of Classification Search
CPC ............ G06V 40/1318; G06V 40/1394; H01L 27/14636; H01L 27/14643; H01L 27/14678; H01L 27/288; A61B 5/02416; A61B 5/1172
USPC ........................................................ 257/200
See application file for complete search history.

(56) References Cited

U.S. PATENT DOCUMENTS 9,312,421 B2    4/2016  Yamada et al.
2002/0079512 A1*  6/2002  Yamazaki ............. H01L 27/288
                                                                                  257/200

FOREIGN PATENT DOCUMENTS

JP            2013-012696 A        1/2013

* cited by examiner

*Primary Examiner* — Abdul-Samad A Adediran
(74) *Attorney, Agent, or Firm* — K&L Gates LLP

(57) ABSTRACT

According to an aspect, a detection device includes: a substrate; a plurality of photoelectric conversion elements provided to the substrate; a plurality of transistors provided corresponding to each of the photoelectric conversion elements; and a plurality of scan lines that extend in a first direction. A plurality of detection elements each include the photoelectric conversion element and the transistors provided so as to overlap the photoelectric conversion element. The detection elements include a first detection element and a second detection element adjacent in a second direction intersecting the first direction, and one of the scan lines is provided between the first detection element and the second detection element and is coupled to the first detection element and the second detection element.

7 Claims, 12 Drawing Sheets

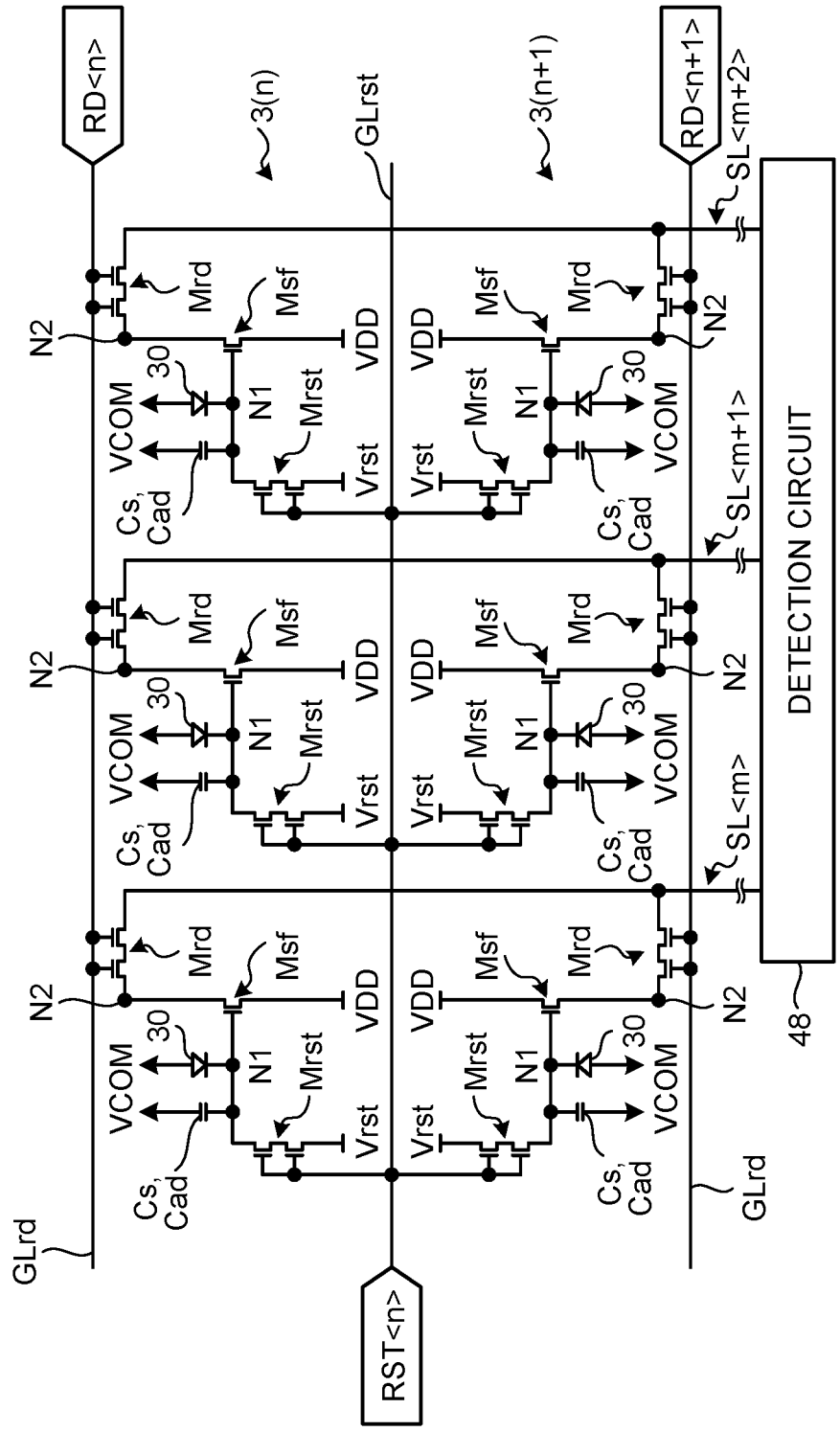

DETECTION DEVICE

CROSS-REFERENCE TO RELATED APPLICATION

This application claims priority from Japanese Application No. 2020-016529, filed on Feb. 3, 2020, the contents of which are incorporated by reference herein in its entirety.

BACKGROUND

1. Technical Field

The present disclosure relates to a detection device.

2. Description of the Related Art

Japanese Patent Application Laid-open Publication No. 2013-12696 (JP-A-2013-12696) describes a detection device (photoelectric conversion device in JP-A-2013-12696) having a plurality of photoelectric conversion elements such as positive-intrinsic-negative (PIN) photodiodes arranged on a substrate. The photoelectric conversion elements of JP-A-2013-12696 are driven by a drive circuit including three transistors and one capacitor. Such an optical detection device is used as, for example, a biometric sensor, such as a fingerprint sensor or a vein sensor, that detects biological information. The photoelectric conversion elements are separately arranged at an arrangement pitch corresponding to a resolution of detection.

The detection device is required to improve the sensor resolution.

SUMMARY

According to an aspect, a detection device includes: a substrate; a plurality of photoelectric conversion elements provided to the substrate; a plurality of transistors provided corresponding to each of the photoelectric conversion elements; and a plurality of scan lines that extend in a first direction. A plurality of detection elements each include the photoelectric conversion element and the transistors provided so as to overlap the photoelectric conversion element. The detection elements include a first detection element and a second detection element adjacent in a second direction intersecting the first direction, and one of the scan lines is provided between the first detection element and the second detection element and is coupled to the first detection element and the second detection element.

BRIEF DESCRIPTION OF THE DRAWINGS

FIG. 4 is a circuit diagram illustrating a plurality of detection elements;

DETAILED DESCRIPTION

Figure 1A:
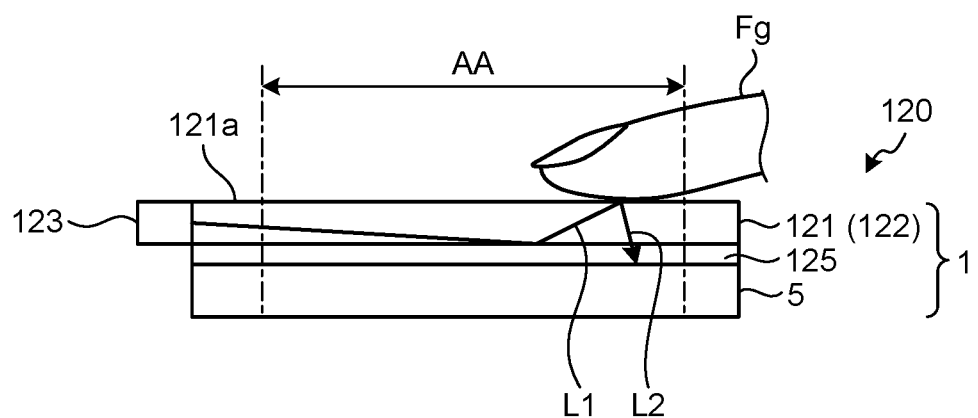
FIG. 1A is a sectional view illustrating a schematic sectional configuration of a detection apparatus having an illumination device, the detection apparatus including a detection device according to a first embodiment of the present disclosure.

The following describes modes (embodiments) for carrying out the present disclosure in detail with reference to the drawings. The present disclosure is not limited to the description of the embodiments given below. Components described below include those easily conceivable by those skilled in the art or those substantially identical thereto. In addition, the components described below can be combined as appropriate. What is disclosed herein is merely an example, and the present disclosure naturally encompasses appropriate modifications easily conceivable by those skilled in the art while maintaining the gist of the disclosure. To further clarify the description, widths, thicknesses, shapes, and the like of various parts may be schematically illustrated in the drawings as compared with actual aspects thereof. However, they are merely examples, and interpretation of the present disclosure is not limited thereto. The same component as that described with reference to an already mentioned drawing is denoted by the same reference numeral through the description and the drawings, and detailed description thereof may not be repeated where appropriate.

In the present specification and claims, in expressing an aspect of disposing another structure on or above a certain structure, a case of simply expressing "on" includes both a case of disposing the other structure immediately on the certain structure so as to contact the certain structure and a case of disposing the other structure above the certain structure with still another structure interposed therebetween, unless otherwise specified.

First Embodiment

Figure 1B:
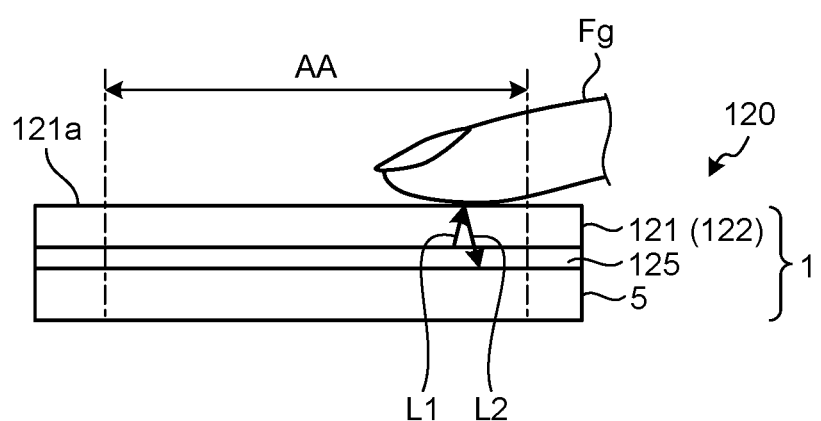
FIG. 1B is a sectional view illustrating a schematic sectional configuration of the detection apparatus having an illumination device, the detection apparatus including the detection device according to a first modification of the first embodiment.
Figure 1C:
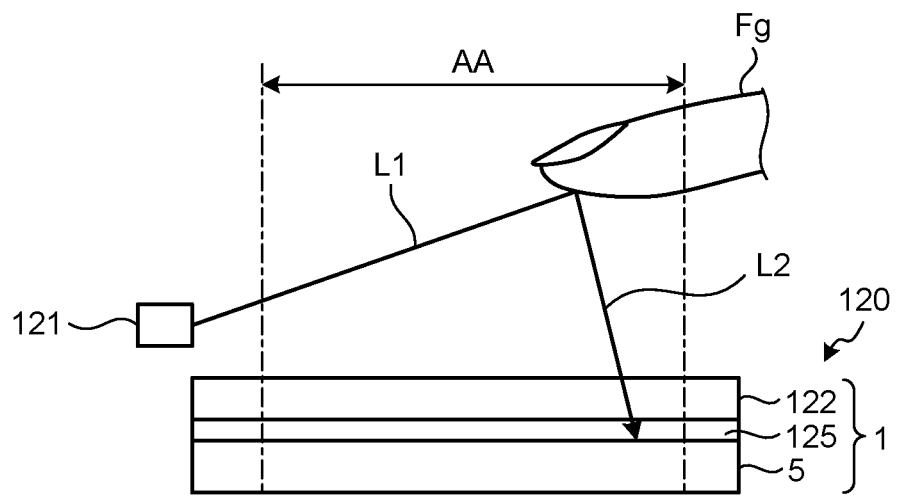
FIG. 1C is a sectional view illustrating a schematic sectional configuration of the detection apparatus having an illumination device, the detection apparatus including the detection device according to a second modification of the first embodiment.
Figure 1D:
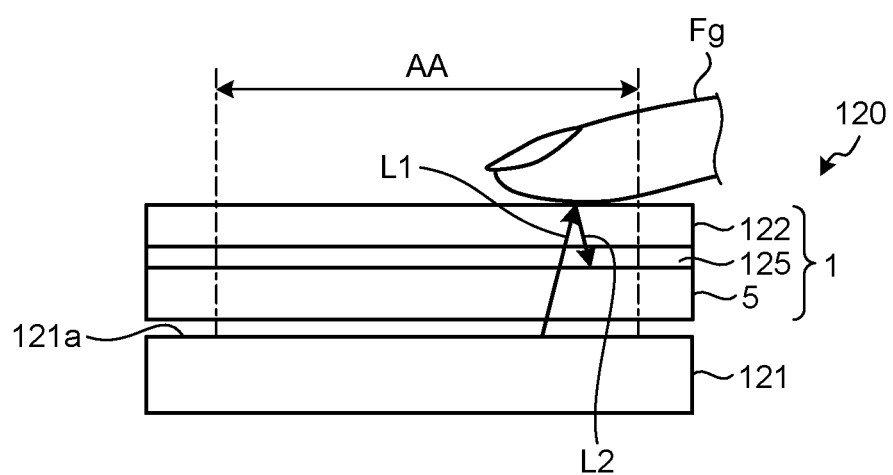
FIG. 1D is a sectional view illustrating a schematic sectional configuration of the detection apparatus having an illumination device, the detection apparatus including the detection device according to a third modification of the first embodiment.

FIG. 1A is a sectional view illustrating a schematic sectional configuration of a detection apparatus having an illumination device, the detection apparatus including a detection device according to a first embodiment of the present disclosure. FIG. 1B is a sectional view illustrating a schematic sectional configuration of the detection apparatus having an illumination device, the detection apparatus including the detection device according to a first modification of the embodiment. FIG. 1C is a sectional view illustrating a schematic sectional configuration of the detection apparatus having an illumination device, the detection apparatus including the detection device according to a second modification of the embodiment. FIG. 1D is a sectional view illustrating a schematic sectional configuration of the detection apparatus having an illumination device, the detection apparatus including the detection device according to a third modification of the embodiment.

As illustrated in FIG. 1A, a detection apparatus 120 having an illumination device includes a detection device 1 and an illumination device 121. The detection device 1 includes a sensor substrate 5, an adhesive layer 125, and a cover member 122. That is, the sensor substrate 5, the adhesive layer 125, and the cover member 122 are stacked in the order as listed, in a direction orthogonal to a surface of the sensor substrate 5. The cover member 122 of the detection device 1 can be replaced with the illumination device 121, as will be described later.

As illustrated in FIG. 1A, the illumination device 121 may be, for example, what is called a side light-type front light that uses the cover member 122 as a light guide plate provided at a location corresponding to a detection region AA of the detection device 1, and that includes a plurality of light sources 123 arranged side by side at one end or both ends of the cover member 122. That is, the cover member 122 has a light-emitting surface 121a for emitting light, and serves as one component of the illumination device 121. The illumination device 121 emits light L1 from the light-emitting surface 121a of the cover member 122 toward a finger Fg serving as a detection target. For example, light-emitting diodes (LEDs), which emit light in a predetermined color, are used as the light sources.

As illustrated in FIG. 1B, the illumination device 121 may include light sources (such as LEDs) provided immediately below the detection region AA of the detection device 1, and the illumination device 121 including the light sources serves also as the cover member 122.

The illumination device 121 is not limited to the example of FIG. 1B. As illustrated in FIG. 1C, the illumination device 121 may be provided on a lateral side of or above the cover member 122, and may emit the light L1 to the finger Fg from the lateral side of or above the finger Fg.

Furthermore, as illustrated in FIG. 1D, the illumination device 121 may be what is called a direct-type backlight that includes light sources (such as LEDs) provided in the detection region AA of the detection device 1.

The light L1 emitted from the illumination device 121 is reflected as light L2 by the finger Fg serving as the detection target. The detection device 1 detects the light L2 reflected by the finger Fg to detect ridges and varies (such as a fingerprint) on the surface of the finger Fg. The detection device 1 may further detect the light L2 reflected inside the finger Fg to detect information on a living body in addition to detecting the fingerprint. Examples of the information on the living body include an image of a blood vessel, such as a vein, pulsation, and a pulse wave. The color of the light L1 from the illumination device 121 may be varied depending on the detection target.

The cover member 122 is a member for protecting the sensor substrate 5, and covers the sensor substrate 5. The illumination device 121 may have a structure to double as the cover member 122 as described above. In the structures illustrated in FIGS. 1C and 1D in which the cover member 122 is separate from the illumination device 121, the cover member 122 is, for example, a glass substrate. The cover member 122 is not limited to the glass substrate, and may be, for example, a resin substrate. The cover member 122 need not be provided. In this case, the surface of the detection device 1 is provided with a protective layer of, for example, an insulating film, and the finger Fg contacts the protective layer of the detection device 1.

As illustrated in FIG. 1B, the detection apparatus 120 having an illumination device may be provided with a display panel instead of the illumination device 121. The display panel may be, for example, an organic electroluminescent (EL) diode (organic light-emitting diode (OLED)) panel or an inorganic EL display (micro-LED or mini-LED) panel. Alternatively, the display panel may be a liquid crystal display (LCD) panel using liquid crystal elements as display elements or an electrophoretic display (EPD) panel using electrophoretic elements as display elements. Also in this case, the fingerprint of the finger Fg and the information on the living body can be detected based on the light L2 resulting from the reflection of the display light (light L1), which has been emitted from the display panel, by the finger Fg.

Figure 2:
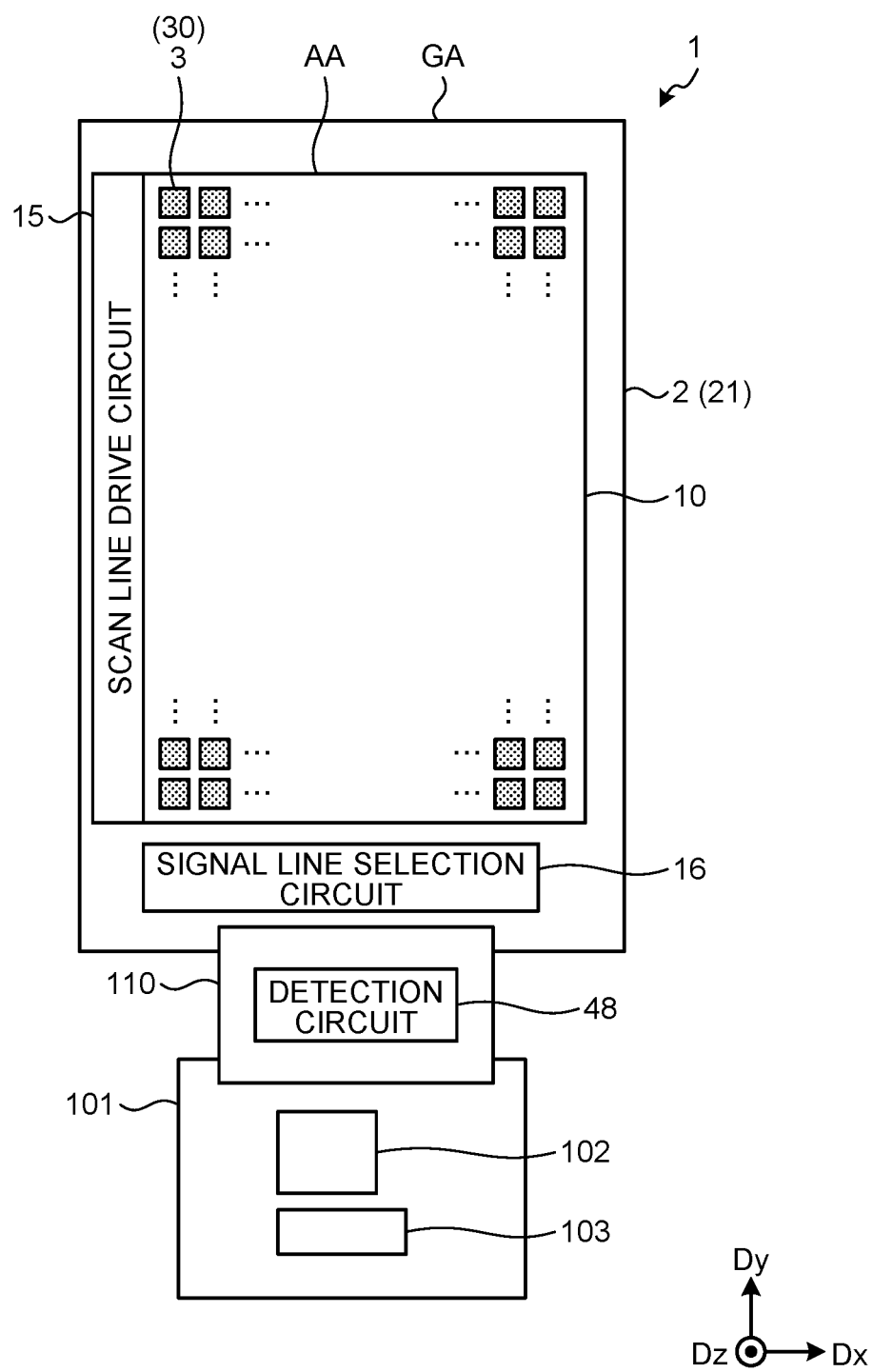
FIG. 2 is a plan view illustrating the detection device according to the first embodiment.

FIG. 2 is a plan view illustrating the detection device according to the first embodiment. As illustrated in FIG. 2, the detection device 1 includes an array substrate 2 (substrate 21), a sensor 10, a scan line drive circuit 15, a signal line selection circuit 16, a detection circuit 48, a control circuit 102, and a power supply circuit 103.

The substrate 21 is electrically coupled to a control substrate 101 through a wiring substrate 110. The wiring substrate 110 is, for example, a flexible printed circuit board or a rigid circuit board. The wiring substrate 110 is provided with the detection circuit 48. The control substrate 101 is provided with the control circuit 102 and the power supply circuit 103. The control circuit 102 is, for example, a field-programmable gate array (FPGA). The control circuit 102 supplies control signals to the sensor 10, the scan line drive circuit 15, and the signal line selection circuit 16 to control detecting operations of the sensor 10. The power supply circuit 103 supplies voltage signals including, for example, a power supply potential VDD and a reference potential VCOM (refer to FIG. 4) to the sensor 10, the scan line drive circuit 15, and the signal line selection circuit 16. Although the present embodiment exemplifies the case of disposing the detection circuit 48 on the wiring substrate 110, the present disclosure is not limited to this case. The detection circuit 48 may be disposed on the substrate 21.

The substrate 21 has the detection region AA and a peripheral region GA. The detection region AA is a region provided with a plurality of detection elements 3 included in the sensor 10. The peripheral region GA is a region outside the detection region AA, and is a region not provided with the detection elements 3. That is, the peripheral region GA is a region between the outer circumference of the detection region AA and outer edges of the substrate 21. The scan line drive circuit 15 and the signal line selection circuit 16 are provided in the peripheral region GA.

Each of the detection elements 3 of the sensor 10 is a photosensor including a photoelectric conversion element 30 as a sensor element. The photoelectric conversion element 30 is a photodiode, and outputs an electrical signal corresponding to light irradiating each of the photoelectric conversion elements 30. More specifically, the photoelectric conversion element 30 is a positive-intrinsic-negative (PIN) photodiode. The detection elements 3 are arranged in a matrix having a row-column configuration in the detection region AA. The photoelectric conversion element 30 included in each of the detection elements 3 performs the detection in accordance with a gate drive signal (for example, a reset control signal RST or a read control signal RD) supplied from the scan line drive circuit 15. Each of the photoelectric conversion elements 30 outputs the electrical signal corresponding to the light irradiating the photoelectric conversion element 30 as a detection signal Vdet to the signal line selection circuit 16. The detection device 1 detects the information on the living body based on the detection signals Vdet received from the photoelectric conversion elements 30.

The scan line drive circuit 15 and the signal line selection circuit 16 are provided in the peripheral region GA. Specifically, the scan line drive circuit 15 is provided in a region extending along a second direction Dy in the peripheral region GA; and the signal line selection circuit 16 is provided in a region extending along a first direction Dx in the peripheral region GA, and is provided between the sensor 10 and the detection circuit 48.

The first direction Dx is one direction in a plane parallel to the substrate 21. The second direction Dy is another direction in the plane parallel to the substrate 21, and is a direction orthogonal to the first direction Dx. The second direction Dy may non-orthogonally intersect the first direction Dx. A third direction Dz is a direction orthogonal to the first direction Dx and the second direction Dy, and is a direction normal to the substrate 21.

Figure 3:
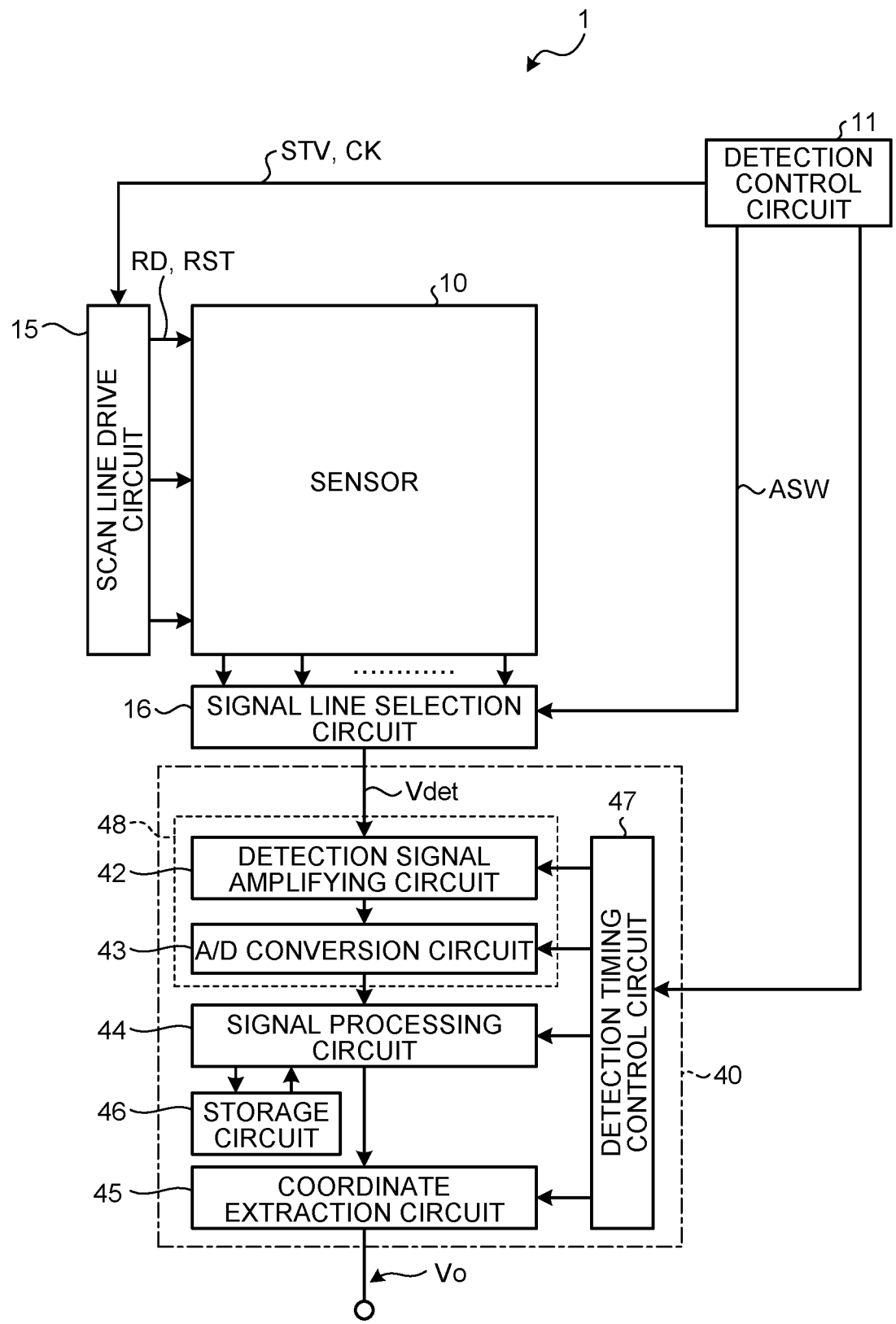
FIG. 3 is a block diagram illustrating a configuration example of the detection device according to the first embodiment.

FIG. 3 is a block diagram illustrating a configuration example of the detection device according to the first embodiment. As illustrated in FIG. 3, the detection device 1 further includes a detection control circuit 11 and a detector 40. One, some, or all functions of the detection control circuit 11 are included in the control circuit 102. One, some, or all functions of the detector 40 other than those of the detection circuit 48 are also included in the control circuit 102.

The detection control circuit 11 supplies control signals to the scan line drive circuit 15, the signal line selection circuit 16, and the detector 40 to control operations of these components. The detection control circuit 11 supplies various control signals including, for example, a start signal STV and a clock signal CK to the scan line drive circuit 15. The detection control circuit 11 also supplies various control signals including, for example, a selection signal ASW to the signal line selection circuit 16.

The scan line drive circuit 15 drives a plurality of scan lines (the read control scan lines GLrd and the reset control scan lines GLrst (refer to FIG. 4)) based on the various control signals. The scan line drive circuit 15 sequentially or simultaneously selects the scan lines and supplies the gate drive signal (for example, the reset control signal RST or the read control signal RD) to the selected scan lines. Through this operation, the scan line drive circuit 15 selects the photoelectric conversion elements 30 coupled to the scan lines.

The signal line selection circuit 16 is a switching circuit that sequentially or simultaneously selects output signal lines SL (refer to FIG. 4). The signal line selection circuit 16 is, for example, a multiplexer. The signal line selection circuit 16 couples the selected output signal lines SL to the detection circuit 48 based on the selection signal ASW supplied from the detection control circuit 11. Through this operation, the signal line selection circuit 16 outputs the detection signal Vdet of the photoelectric conversion element 30 to the detector 40.

The detector 40 includes the detection circuit 48, a signal processing circuit 44, a coordinate extraction circuit 45, a storage circuit 46, and a detection timing control circuit 47. The detection timing control circuit 47 performs control to cause the detection circuit 48, the signal processing circuit 44, and the coordinate extraction circuit 45 to operate in synchronization with one another based on a control signal supplied from the detection control circuit 11.

The detection circuit 48 is, for example, an analog front end (AFE) circuit. The detection circuit 48 is a signal processing circuit having functions of at least a detection signal amplifying circuit 42 and an analog-to-digital (A/D) conversion circuit 43. The detection signal amplifying circuit 42 is a circuit that amplifies the detection signal Vdet, and is, for example, an integration circuit. The A/D conversion circuit 43 converts an analog signal output from the detection signal amplifying circuit 42 into a digital signal.

The signal processing circuit 44 is a logic circuit that detects a predetermined physical quantity received by the sensor 10 based on output signals of the detection circuit 48. The signal processing circuit 44 can detect ridges and varies on a surface of the finger Fg or a palm based on the signals from the detection circuit 48 when the finger Fg is in contact with or in proximity to a detection surface. The signal processing circuit 44 may detect the information on the living body based on the signals from the detection circuit 48. Examples of the information on the living body include an image of a blood vessel of the finger Fg or the palm, a pulse wave, pulsation, and blood oxygen saturation.

The storage circuit 46 temporarily stores therein signals calculated by the signal processing circuit 44. The storage circuit 46 may be, for example, a random-access memory (RAM) or a register circuit.

The coordinate extraction circuit 45 is a logic circuit that obtains detected coordinates of the ridges and varies on the surface of the finger Fg or the like when the contact or proximity of the finger Fg is detected by the signal processing circuit 44. The coordinate extraction circuit 45 is the logic circuit that also obtains detected coordinates of blood vessels of the finger Fg or the palm. The coordinate extraction circuit 45 combines the detection signals Vdet output from the respective detection elements 3 of the sensor 10 to generate two-dimensional information representing a shape of the ridges and varies on the surface of the finger Fg or the like. The coordinate extraction circuit 45 may output the detection signals Vdet as sensor outputs Vo instead of calculating the detected coordinates.

The following describes a circuit configuration example of the detection device 1. FIG. 4 is a circuit diagram illustrating the detection elements. As illustrated in FIG. 4, each of the detection elements 3 includes the photoelectric conversion element 30, a reset transistor Mrst, a read transistor Mrd, and a source follower transistor Msf. The detection elements 3 are provided with the reset control scan lines GLrst and the read control scan lines GLrd as detection drive lines (scan lines), and provided with the output signal lines SL as wiring for reading signals.

Each of the reset control scan lines GLrst, the read control scan lines GLrd, and the output signal line SL is coupled to the detection elements 3. Specifically, the reset control scan lines GLrst and the read control scan lines GLrd extend in the first direction Dx (refer to FIG. 2), and are each coupled to the detection elements 3 arranged in the first direction Dx; and the output signal lines SL extend in the second direction Dy, and are each coupled to the detection elements 3 arranged in the second direction Dy.

The reset transistor Mrst, the read transistor Mrd, and the source follower transistor Msf are provided corresponding to each of the photoelectric conversion elements 30. Each of the transistors included in the detection element 3 is made up of an n-type thin-film transistor (TFT). However, each of the transistors is not limited thereto, and may be made up of a p-type TFT.

The reference potential VCOM is applied to an anode of the photoelectric conversion element 30. A cathode of the photoelectric conversion element 30 is coupled to a node N1. The node N1 is coupled to a capacitor Cs, a capacitor Cad, one of the source and the drain of the reset transistor Mrst, and the gate of the source follower transistor Msf. one end of each of the capacitors Cs and Cad is coupled to the node N1, and the other end thereof is coupled to the reference potential VCOM. When light irradiates the photoelectric conversion element 30, a signal (electrical charge) output from the photoelectric conversion element 30 is stored in the capacitors Cs and Cad.

Although FIG. 4 illustrates the capacitors Cad and Cs as one element, the capacitors Cad and Cs are actually made up of capacitors formed between different sets of electrodes. The capacitor Cs is, for example, a capacitor formed between an upper electrode 34 and a lower electrode 35 coupled to the photoelectric conversion element 30 (refer to FIG. 8). The capacitor Cad is a capacitor added to the capacitor Cs, and is a capacitor formed between a first electrode 81 and a second electrode 82 provided in the array substrate 2 (refer to FIG. 8).

The gates of the reset transistor Mrst are coupled to the reset control scan line GLrst. The other one of the source and the drain of the reset transistor Mrst is supplied with a reset potential Vrst. When the reset transistor Mrst is turned on (into a conduction state) in response to the reset control signal RST, the potential of the node N1 is reset to the reset potential Vrst. The reference potential VCOM is lower than the reset potential Vrst, and the photoelectric conversion element 30 is driven in a reverse bias state.

The source follower transistor Msf is coupled between a terminal supplied with the power supply potential VDD and the read transistor Mrd (node N2). The gate of the source follower transistor Msf is coupled to the node N1. The gate of the source follower transistor Msf is supplied with the signal (electrical charge) generated by the photoelectric conversion element 30. This operation causes the source follower transistor Msf to output a signal (voltage) corresponding to the signal (electrical charge) generated by the photoelectric conversion element 30 to the read transistor Mrd.

The read transistor Mrd is coupled between the source of the source follower transistor Msf (node N2) and the output signal line SL. The gates of the read transistor Mrd are coupled to the read control scan line GLrd. When the read transistor Mrd is turned on in response to the read control signal RD, the signal output from the source follower transistor Msf, that is, the signal voltage corresponding to the signal (electrical charge) generated by the photoelectric conversion element 30 is output as the detection signal Vdet to the output signal line SL.

Assume that detection elements 3(n) denote the detection elements 3 belonging to the n-th row, and detection elements 3(n+1) denote the detection elements 3 belonging to the (n+1)-th row. One of the reset control scan lines GLrst is coupled to the detection elements 3(n) and the detection elements 3(n+1) adjacent to each other in the second direction Dy. That is, the one of the reset control scan lines GLrst is shared by the detection elements 3(n) and the detection elements 3(n+1) adjacent to each other in the second direction Dy. This configuration causes the common reset control signal RST to be supplied to the detection elements 3(n) and the detection elements 3(n+1).

In the example illustrated in FIG. 4, the reset transistor Mrst and the read transistor Mrd each have what is called a double-gate structure configured by coupling two transistors in series. However, the structures of those transistors are not limited thereto; the reset transistor Mrst and the read transistor Mrd may have a single-gate structure or a structure configured by coupling three or more transistors in series. The circuit of each of the detection elements 3 is not limited to the configuration including the three transistors of the reset transistor Mrst, the source follower transistor Msf, and the read transistor Mrd. The detection element 3 may have two transistors or four or more transistors.

Figure 5A:
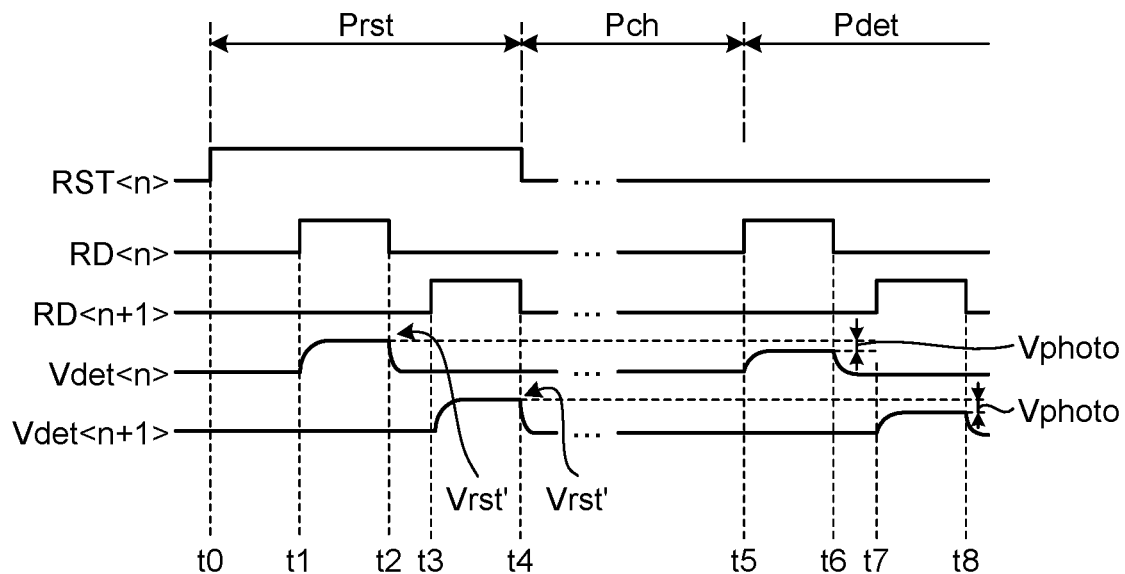
FIG. 5A is a timing waveform diagram illustrating an operation example of the detection elements.

FIG. 5A is a timing waveform diagram illustrating an operation example of the detection elements. As illustrated in FIG. 5A, the detection elements 3 perform the detection in the order of a reset period Prst, a storage period Pch, and a read period Pdet. The power supply circuit 103 supplies the reference potential VCOM to the anodes of the photoelectric conversion elements 30 over the reset period Prst, the storage period Pch, and the read period Pdet.

At time t0, the control circuit 102 sets the reset control signal RST to be supplied to the reset control scan lines GLrst to HIGH (high-level voltage) to start the reset period Prst. In the reset period Prst, each of the reset transistors Mrst belonging to the detection elements 3(n) and the detection elements 3(n+1) is turned on (into the conduction state) based on the reset control signal RST. This operation increases the potential of the node N1 to the reset potential Vrst. The read transistor Mrd is off (in a nonconduction state). Hence, one of the source and the drain of the source follower transistor Msf is charged by the power supply potential VDD to increase the potential of the node N2.

At time t1, the control circuit 102 sets the read control signal RD(n) to be supplied to the read control scan line GLrd(n) of the detection elements 3(n) to HIGH (high-level voltage). As a result, the read transistor Mrd of each of the detection elements 3(n) is turned on (into the conduction state) to set the potential of the node N2 to (the reset potential Vrst−a threshold potential Vth (Msf) of the source follower transistor). At time t2, the potential of the detection signal Vdet(n) output from the output signal line SL reaches a potential Vrst' corresponding to the reset potential Vrst.

At time t2, the control circuit 102 sets the read control signal RD(n) to LOW (low-level voltage). As a result, the read transistor Mrd of each of the detection elements 3(n) is turned off (into the nonconduction state). A load is applied so as to set the potential of the detection signal Vdet(n) output from the output signal line SL to LOW (low-level voltage).

In the same way, at time t3, the control circuit 102 sets the read control signal RD(n+1) to be supplied to the read control scan line GLrd(n+1) of the detection elements 3(n+1) to HIGH (high-level voltage). As a result, the read transistor Mrd of each of the detection elements 3(n+1) is turned on (into the conduction state) to set the potential of the node N2 to (the reset potential Vrst−the threshold potential Vth (Msf) of the source follower transistor). At time t4, the potential of the detection signal Vdet(n+1) output from the output signal line SL reaches the potential Vrst' corresponding to the reset potential Vrst.

At time t4, the control circuit 102 sets the read control signal RD(n+1) to LOW (low-level voltage). As a result, the read transistor Mrd of each of the detection elements 3(n+1)

is turned off (into the nonconduction state). A load is applied so as to set the potential of the detection signal Vdet(n+1) output from the output signal line SL to LOW (low-level voltage).

At time t4, the control circuit 102 sets the reset control signal RST to LOW (low-level voltage) to end the reset period Prst and start the storage period Pch. In the storage period Pch, the reset transistor Mrst is turned off (into the nonconduction state). The signal corresponding to the light irradiating the photoelectric conversion element 30 is stored to reduce the potential of the node N1 to (Vrst−Vphoto). Vphoto denotes a signal (voltage change amount) corresponding to the light irradiating the photoelectric conversion element 30.

At time t5, the control circuit 102 sets the read control signal RD(n) to HIGH (high-level voltage). As a result, the read transistor Mrd of each of the detection elements 3(n) is turned on (into the conduction state) to end the storage period Pch and start the read period Pdet. The potential of the node N2 changes to (Vrst'−Vphoto) in response to the signal Vphoto. The potential of the detection signal Vdet(n) output at time t6 in the read period Pdet decreases by an amount of the signal Vphoto from the potential of the detection signal Vdet(n) obtained at time t2.

The detector 40 can detect the light irradiating the photoelectric conversion element 30 belonging to the detection element 3(n) based on the signal Vphoto of the difference between the detection signal Vdet(n) at time t2 and the detection signal Vdet(n) at time t6.

In the same way, at time t7, the control circuit 102 sets the read control signal RD(n+1) to HIGH (high-level voltage). As a result, the read transistor Mrd of each of the detection elements 3(n+1) is turned on (into the conduction state). The potential of the node N2 changes to (Vrst−Vphoto) in response to the signal Vphoto. The potential of the detection signal Vdet(n+1) output at time t8 in the read period Pdet decreases by the amount of the signal Vphoto from the potential of the detection signal Vdet(n+1) obtained at time t4.

The detector 40 can detect the light irradiating the photoelectric conversion element 30 belonging to the detection element 3(n+1) based on the signal Vphoto of the difference between the detection signal Vdet(n+1) at time t4 and the detection signal Vdet(n+1) at time t8.

Figure 5B:
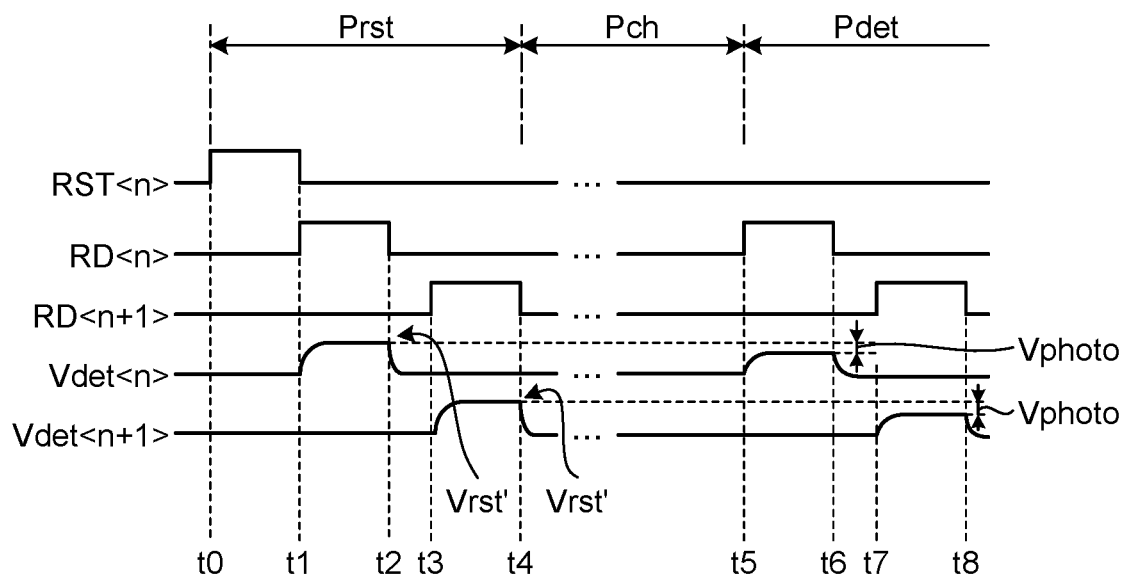
FIG. 5B is a timing waveform diagram illustrating an operation example of the detection elements according to a fourth modification of the first embodiment.

FIG. 5A illustrates the operation example of the detection elements 3(n) and 3(n+1), where the scan line drive circuit 15 sequentially scans each of the reset control scan lines GLrst and the read control scan lines GLrd in a time division manner so as to be capable of causing the detection elements 3 in the entire detection region AA to perform the detection. Although the control circuit 102 keeps the reset control signal RST at HIGH (high-level voltage) over the period from time t0 to time t4 in the reset period Prst, the present disclosure is not limited thereto. FIG. 5B is a timing waveform diagram illustrating an operation example of the detection elements according to a fourth modification of the first embodiment. As illustrated in FIG. 5B, the control circuit 102 may set the reset control signal RST to LOW before time t1 and sequentially set the read control signals RD(n) and RD(n+1) to HIGH after the reset control signal RST has fallen.

In the present embodiment, the capacitor Cad is added in addition to the capacitor Cs. Consequently, the potential of the node N1 is restrained from decreasing in the storage period Pch. Hence, the potential of the node N1 is restrained from fluctuating. As a result, the signal (voltage) output from the source follower transistor Msf in the read period Pdet is restrained from fluctuating.

Figure 6:
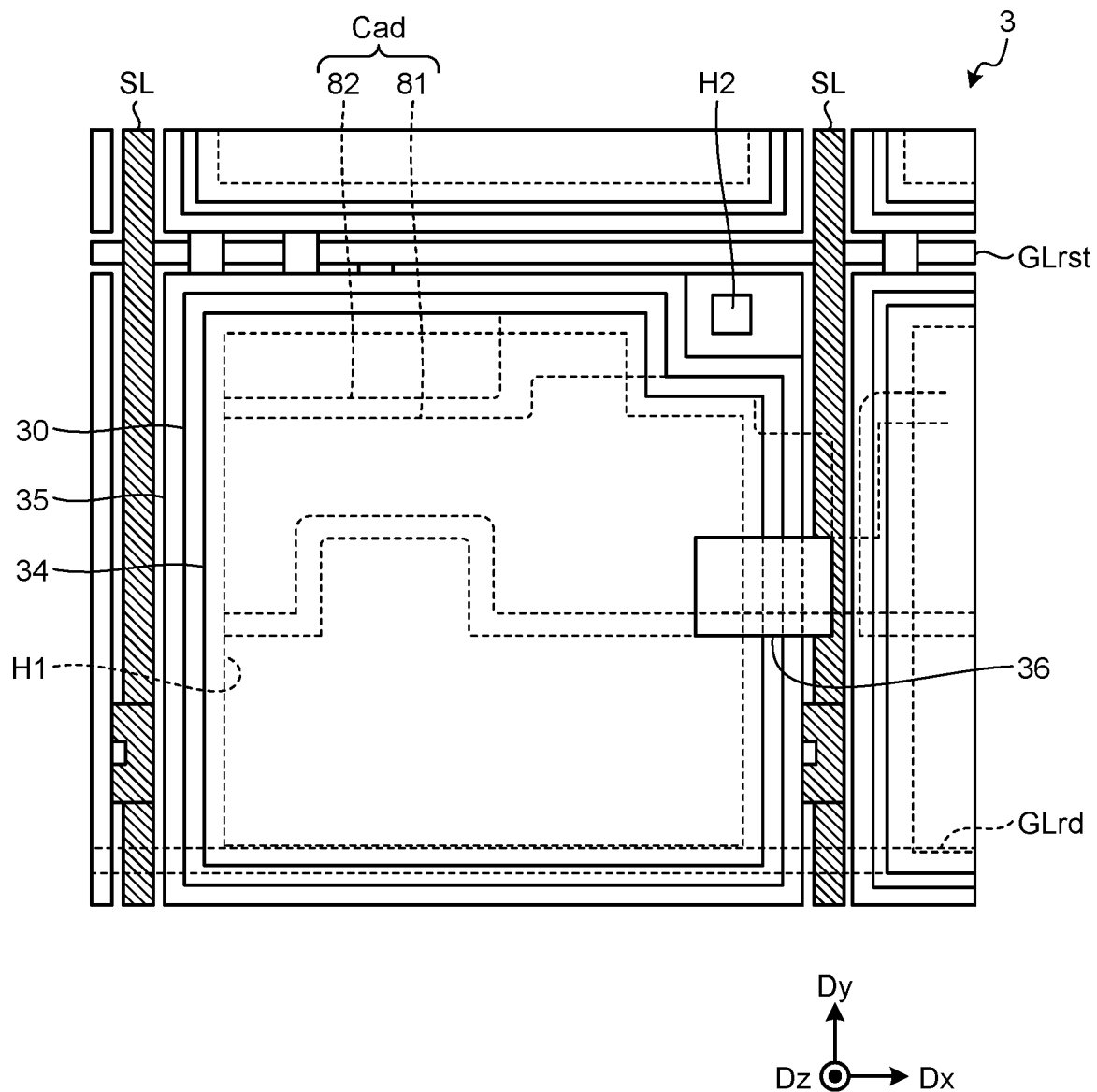
FIG. 6 is a plan view illustrating the detection element.

The following describes a planar configuration and a sectional configuration of the detection element 3. FIG. 6 is a plan view illustrating the detection element. As illustrated in FIG. 6, each of the detection elements 3 is formed in a region surrounded by the reset control scan line GLrst, the read control scan line GLrd, and two of the output signal lines SL.

The reset control scan lines GLrst and the read control scan lines GLrd each extend in the first direction Dx, and are arranged in the second direction Dy. The output signal lines SL each extend in the second direction Dy, and are arranged in the first direction Dx.

The photoelectric conversion element 30 is provided in a region surrounded by the reset control scan line GLrst and the read control scan line GLrd adjacent in the second direction Dy and two of the output signal lines SL adjacent in the first direction Dx. The photoelectric conversion element 30 is provided so as to overlap a portion of the read control scan line GLrd.

The upper electrode 34 and the lower electrode 35 face each other in the third direction Dz with the photoelectric conversion element 30 interposed therebetween. Specifically, the photoelectric conversion element 30 is disposed above the array substrate 2 provided with various types of wiring and various transistors, with the lower electrode 35 interposed therebetween.

The lower electrode 35 has a larger area than the photoelectric conversion element 30 and the upper electrode 34 have. The lower electrode 35 is electrically coupled, at a portion thereof overlapping neither the photoelectric conversion element 30 nor the upper electrode 34, to the reset transistor Mrst and the source follower transistor Msf through a contact hole H2. The upper electrode 34 is provided so as to cover the photoelectric conversion element 30, and is electrically coupled to the photoelectric conversion element 30 through a contact hole H1. The upper electrode 34 is coupled to a reference potential supply line through coupling wiring 36, and supplies the reference potential VCOM to the photoelectric conversion element 30. The reference potential supply line is not illustrated, but is provided, for example, so as to extend in the second direction Dy overlapping the output signal line SL.

The first and second electrodes 81 and 82 are provided in a region overlapping the photoelectric conversion element 30. The capacitor Cad is formed between the first and second electrodes 81 and 82. A detailed configuration of the photoelectric conversion element 30 and the first and second electrodes 81 and 82 will be described later.

Figure 7:
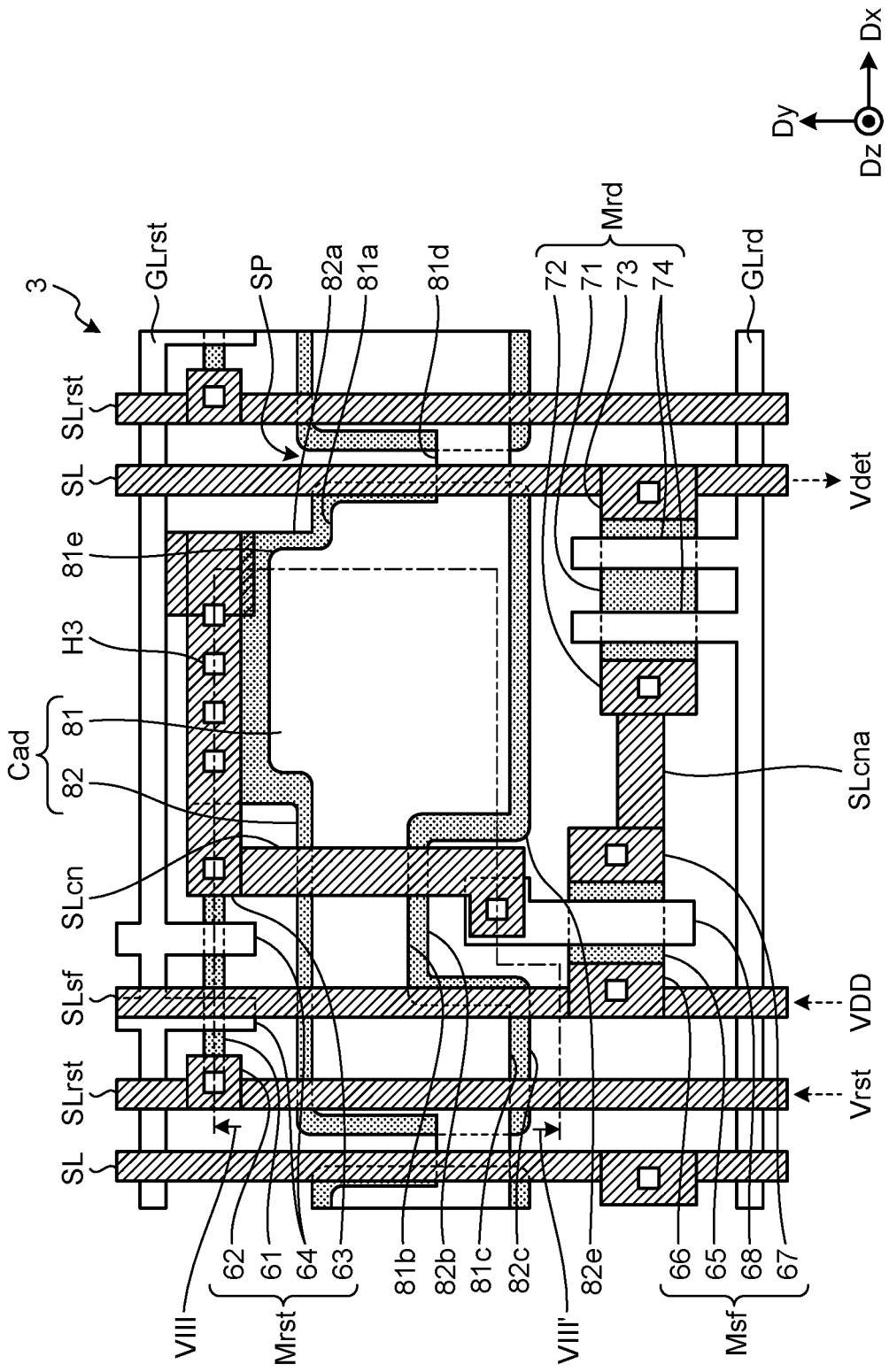
FIG. 7 is a plan view of an array substrate on which the detection element is formed.

FIG. 7 is a plan view of the array substrate on which the detection element is formed. FIG. 7 is a plan view schematically illustrating a portion of the detection element 3, that is, a portion thereof except members on the upper side of the photoelectric conversion element 30.

As illustrated in FIG. 7, in the detection element 3, the photoelectric conversion element 30, the transistors, and the capacitor Cad are provided between the reset control scan line GLrst and the read control scan line GLrd adjacent in the second direction Dy. A power supply signal line SLsf and a reset signal line SLrst each extend in the second direction Dy, and are arranged in the first direction Dx with the output signal line SL.

The photoelectric conversion element 30 illustrated in FIG. 6 is disposed on the array substrate 2 provided with the various types of wiring and the various transistors, overlaps at least a portion of the various transistors, and is provided in a region overlapping at least a portion of the power supply signal line SLsf, the reset signal line SLrst, and the read control scan line GLrd.

As illustrated in FIG. 7, the reset transistor Mrst includes a semiconductor layer 61, a source electrode 62, a drain electrode 63, and gate electrodes 64. One end of the semiconductor layer 61 is coupled to the reset signal line SLrst. The other end of the semiconductor layer 61 is coupled to coupling wiring SLcn. A portion of the reset signal line SLrst coupled to the semiconductor layer 61 serves as the source electrode 62, and a portion of the coupling wiring SLcn coupled to the semiconductor layer 61 serves as the drain electrode 63. The reset control scan line GLrst is provided with two branches branching in the second direction Dy, and the semiconductor layer 61 intersects the two branches of the reset control scan line GLrst. The two branches are provided adjacent to each other in the first direction Dx. Portions of the two branches of the reset control scan line GLrst overlapping the semiconductor layer 61 serve as the gate electrodes 64. Channel regions are formed at portions of the semiconductor layer 61 overlapping the two branches of the reset control scan line GLrst.

The coupling wiring SLcn is formed in an inverted L-shape and includes a portion extending in the first direction Dx and a portion extending in the second direction Dy. An end of the portion of the coupling wiring SLcn extending in the first direction Dx is coupled to the cathode (n-type semiconductor layer 33) of the photoelectric conversion element 30 through the contact hole H2 (refer to FIG. 6). The reset transistor Mrst is coupled to the gate of the source follower transistor Msf through the portion of the coupling wiring SLcn extending in the second direction Dy. That is, the coupling wiring SLcn corresponds to the node N1 in FIG. 4.

The source follower transistor Msf includes a semiconductor layer 65, a source electrode 67, a drain electrode 66, and a gate electrode 68. One end of the semiconductor layer 65 is coupled to the power supply signal line SLsf. The other end of the semiconductor layer 65 is coupled to the read transistor Mrd through coupling wiring SLcna. A portion of the power supply signal line SLsf coupled to the semiconductor layer 65 serves as the drain electrode 66, and a portion of the coupling wiring SLcna coupled to the semiconductor layer 65 serves as the source electrode 67.

One end of the gate electrode 68 is coupled to the coupling wiring SLcn through a contact hole. The semiconductor layer 65 intersects the gate electrode 68. A channel region is formed at a portion of the semiconductor layer 65 intersecting the gate electrode 68.

The above-described configuration electrically couples the cathode (n-type semiconductor layer 33) of the photoelectric conversion element 30 to the reset transistor Mrst and the source follower transistor Msf through the coupling wiring SLcn.

The read transistor Mrd includes a semiconductor layer 71, a source electrode 73, a drain electrode 72, and gate electrodes 74. One end of the semiconductor layer 71 is coupled to the source follower transistor Msf through the coupling wiring SLcna. The other end of the semiconductor layer 71 is coupled to the output signal line SL. A portion of the output signal line SL coupled to the semiconductor layer 71 serves as the source electrode 73. A portion of the coupling wiring SLcna coupled to the semiconductor layer 71 serves as the drain electrode 72. Two branches extending in the second direction Dy are coupled to the read control scan line GLrd. The two branches are provided adjacent to each other in the first direction Dx. The semiconductor layer 71 intersects the two branches branching from the read control scan line GLrd. The two branches of the read control scan line GLrd serve as the gate electrodes 74. The above-described configuration couples the source follower transistor Msf and the read transistor Mrd to the output signal line SL.

The first and second electrodes 81 and 82 are provided in a region in a plan view that overlaps the photoelectric conversion element 30 and overlaps none of the reset transistor Mrst, the source follower transistor Msf, and the read transistor Mrd. The first electrode 81 includes a main part 81a, a coupling part 81b, a sub-part 81c, and a connecting part 81d. The second electrode 82 includes a main part 82a, a coupling part 82b, and a sub-part 82c. The main parts 81a and 82a are provided so as to overlap each other. The coupling part 81b and the coupling part 82b are provided so as to overlap each other. The sub-part 81c and the sub-part 82c are provided so as to overlap each other.

The main parts 81a and 82a are respectively formed so as to have the largest areas among those of the parts constituting the first and second electrodes 81 and 82, and are provided in a region surrounded by the output signal line SL, the coupling wiring SLcn, the source follower transistor Msf, and the read transistor Mrd. The second electrode 82 is coupled, at an end on the second direction Dy side of the main part 82a, to a portion of the coupling wiring SLcn extending in first direction Dx through four contact holes H3. This configuration electrically couples the second electrode 82 through the coupling wiring SLcn (node N1) to the cathode of the photoelectric conversion element 30, the reset transistor Mrst, and the gate of the source follower transistor Msf.

The coupling parts 81b and 82b are provided so as to overlap the portion of the coupling wiring SLcn extending in the second direction Dy. The coupling part 81b couples together the main part 81a and the sub-part 81c adjacent to each other in the first direction Dx. The coupling part 82b couples together the main part 82a and the sub-part 82c adjacent to each other in the first direction Dx. Widths of the coupling parts 81b and 82b in the second direction Dy are less than those of the main parts 81a and 82a in the second direction Dy.

The sub-parts 81c and 82c are provided between the reset signal line SLrst and the power supply signal line SLsf. Widths of the sub-parts 81c and 82c in the second direction Dy are greater than those of the coupling parts 81b and 82b in the second direction Dy.

The connecting part 81d couples together the main part 81a and the sub-part 81c of the first electrode 81 adjacent in the first direction Dx. In other words, the first electrode 81 extends in the first direction Dx so as to overlap the detection elements 3 arranged in the first direction Dx. The first electrode 81 is coupled to the reference potential VCOM at any place. The second electrode 82 is separately provided for each of the detection elements 3.

With the above-described configuration, the first and second electrodes 81 and 82 form a capacitor between the main parts 81a and 82a facing each other, and further form capacitors between the coupling parts 81b and 82b facing each other and between the sub-parts 81c and 82c facing each other, thus forming the large capacitor Cad as a whole. However, the first and second electrodes 81 and 82 are not limited to this configuration, and may be without the coupling parts 81b and 82b and the sub-parts 81c and 82c.

The first and second electrodes 81 and 82 have eased portions 81e and 82e obtained by easing corners. That is, no sharp portion is formed at ends of the first and second electrodes 81 and 82. Consequently, concentration of electric fields at the ends of the first and second electrodes 81 and 82 can be more reduced than a case where the corners of the first and second electrodes 81 and 82 are formed to have right angles. As a result, generation of an electrostatic discharge (ESD) can be restrained in the manufacturing process of the array substrate 2 of the detection device 1.

The planar configuration of the photoelectric conversion element 30, the capacitor Cad, and the transistors illustrated in FIGS. 6 and 7 is merely an example, and can be changed as appropriate. For example, the arrangement of the transistors may be varied. For example, although the semiconductor layer 65 and the semiconductor layer 71 are separately disposed in the present embodiment, the present disclosure is not limited thereto. The source follower transistor Msf and the read transistor Mrd may be formed of one common semiconductor layer.

The arrangement of the first and second electrodes 81 and 82 may be changed as appropriate depending on the arrangement of the transistors. In FIGS. 6 and 7, the area of the second electrode 82 is provided to be larger than that of the first electrode 81, and the second electrode 82 is disposed such that the outer circumference of the second electrode 82 surrounds the circumference of the first electrode 81. However, the present disclosure is not limited to this arrangement. The relation between the areas of the second electrode 82 and the first electrode 81 may be reversed, or the areas may be the same as each other.

Figure 8:
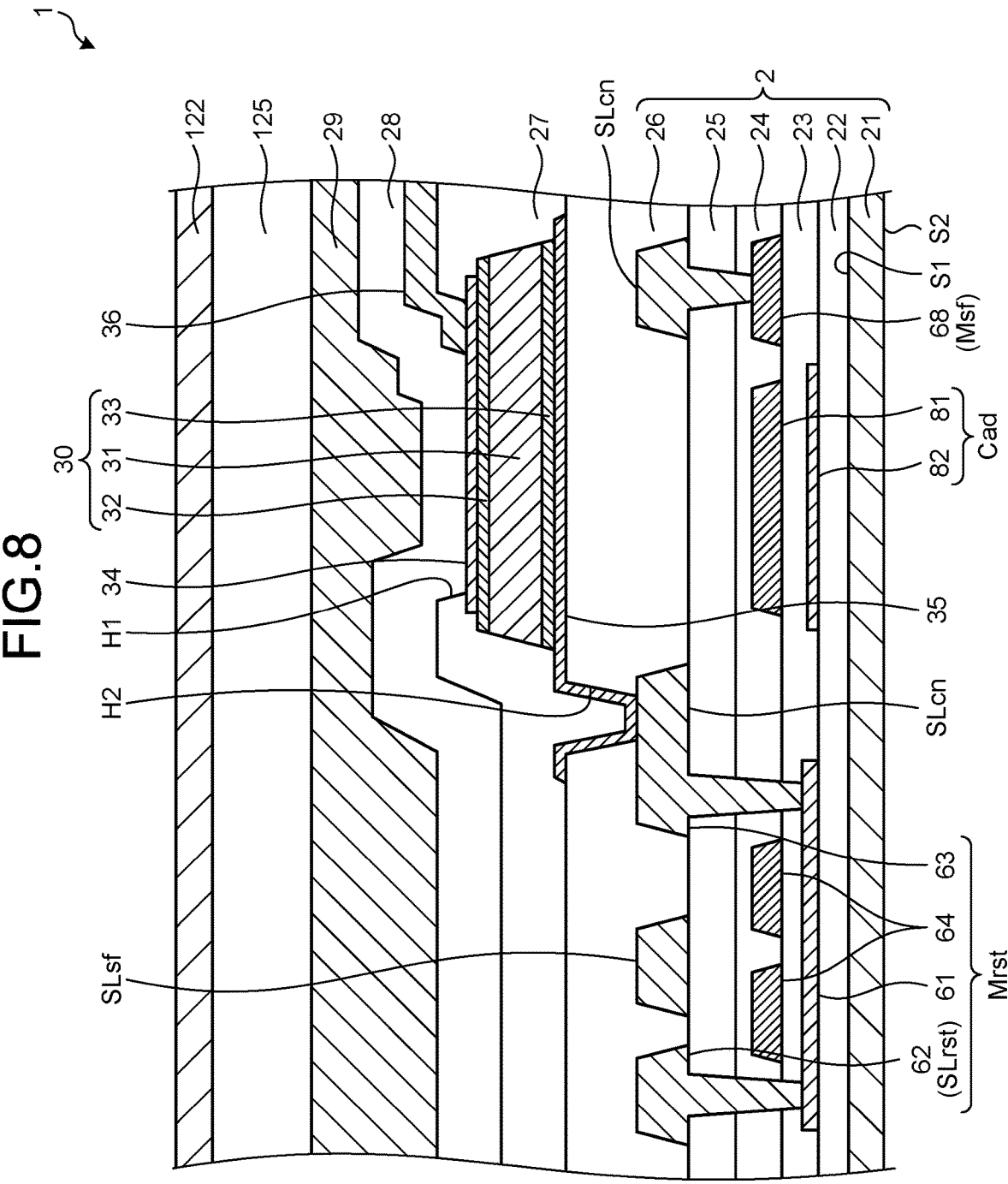
FIG. 8 is an VIII-VIII' sectional view of FIG. 7.

FIG. 8 is a VIII-VIII' sectional view of FIG. 7. While FIG. 8 illustrates a sectional configuration of the reset transistor Mrst among the three transistors included in the detection element 3, each of the source follower transistor Msf and the read transistor Mrd also has a sectional configuration similar to that of the reset transistor Mrst.

The substrate 21 is an insulating substrate, and a glass substrate of, for example, quartz or alkali-free glass is used as the substrate 21. The substrate 21 has a first principal surface S1 and a second principal surface S2 on the opposite side of the first principal surface S1. The first principal surface S1 of the substrate 21 is provided with various transistors including the reset transistor Mrst, various types of wiring (the scan lines and the signal lines), the first electrodes 81, the second electrode 82, and insulating films to form the array substrate 2. The photoelectric conversion element 30 is arranged on the array substrate 2, that is, on the first principal surface S1 side of the substrate 21.

An undercoat film 22 is provided on the first principal surface S1 of the substrate 21. The undercoat film 22, insulating films 23, 24, and 25, and an insulating film 27 are inorganic insulating films, and are formed of, for example, a silicon oxide (SiO$_2$) or a silicon nitride (SiN).

In the sectional configuration of the reset transistor Mrst, the semiconductor layer 61 is provided on the undercoat film 22. For example, polysilicon is used as the semiconductor layer 61. The semiconductor layer 61 is, however, not limited thereto, and may be formed of, for example, a microcrystalline oxide semiconductor, an amorphous oxide semiconductor, or low-temperature polycrystalline silicon (LTPS).

The insulating film 23 is provided on the undercoat film 22 so as to cover the semiconductor layer 61. The gate electrodes 64 are provided on the insulating film 23. The gate electrode 68 of the source follower transistor Msf is also provided in the same layer as that of the gate electrodes 64 on the insulating film 23. The insulating film 23 is a gate insulating film. Tetraethyl orthosilicate (TEOS) can be used as a material of the insulating film 23. The reset control scan line GLrst and the read control scan line GLrd (refer to FIG. 6) are also provided in the same layer as that of the gate electrodes 64. The insulating film 24 is provided on the insulating film 23 so as to cover the gate electrodes 64 and 68.

The reset transistor Mrst has a top-gate structure in which the gate electrodes 64 are provided on the upper side of the semiconductor layer 61. However, the reset transistor Mrst may have a bottom-gate structure in which the gate electrodes 64 are provided on the lower side of the semiconductor layer 61, or a dual-gate structure in which the gate electrodes 64 are provided on the upper side and lower side of the semiconductor layer 61.

The insulating films 24 and 25 are provided on the insulating film 23 so as to cover the gate electrodes 64. The source electrode 62 and the drain electrode 63 are provided on the insulating film 25. The source electrode 62 and the drain electrode 63 are each coupled to the semiconductor layer 61 through a contact hole penetrating the insulating films 23, 24, and 25. The source electrode 62 and the drain electrode 63 are formed of, for example, a multilayered film Ti—Al—Ti or Ti—Al having a multilayered structure of titanium and aluminum.

The various signal lines (the output signal line SL (refer to FIG. 6), the power supply signal line SLsf, and the reset signal line SLrst) and the coupling wiring SLcn are provided in the same layer as that of the source electrode 62 and the drain electrode 63. The coupling wiring SLcn is coupled to the gate electrode 68 of the source follower transistor Msf through a contact hole penetrating the insulating films 24 and 25.

The first and second electrodes 81 and 82 forming the capacitor Cad are provided using two of the layers constituting the transistors (for example, the reset transistor Mrst). In the present embodiment, the first and second electrodes 81 and 82 are provided between the substrate 21 and the photoelectric conversion element 30 in the third direction Dz. The second electrode 82 is provided on the undercoat film 22, and faces the first electrode 81 with the insulating film 23 interposed therebetween in the third direction Dz. The first electrode 81 is in the same layer as that of the gate electrodes 64, and is formed of the same material as that of the gate electrodes 64. The second electrode 82 is in the same layer as that of the semiconductor layer 61, and is formed of the same material as that of the semiconductor layer 61.

Since the first and second electrodes 81 and 82 are provided in the same layer as that of the reset transistor Mrst, the manufacturing process is simpler and the detection device 1 (array substrate 2) can be thinner than in a configuration in which the capacitor Cad is formed in a layer different from that of the reset transistor Mrst.

The layers in which the first and second electrodes 81 and 82 are provided are not limited to the example illustrated in FIG. 8. One of the first and second electrodes 81 and 82 may be provided, for example, in the same layer as that of the source electrode 62 and the drain electrode 63. Alternatively, the first and second electrodes 81 and 82 may be provided on the upper side of the array substrate 2 and provided in layers between the photoelectric conversion element 30 and the cover member 122.

An insulating film 26 is provided on the insulating film 25 so as to cover the various transistors including, for example, the reset transistor Mrst, and the capacitor Cad. The insulating film 26 is formed of an organic material such as a photosensitive acrylic resin. The insulating film 26 is thicker than the insulating film 25. The insulating film 26 has a better step covering property than that of inorganic insulating materials, and can planarize steps formed by the various transistors and the various types of wiring.

The following describes sectional configurations of the photoelectric conversion element 30. The photoelectric conversion element 30 is provided on the upper side of the insulating film 26. Specifically, the lower electrode 35 is provided on the insulating film 26, and is electrically coupled to the coupling wiring SLcn through the contact hole H2. The photoelectric conversion element 30 is coupled to the lower electrode 35. The lower electrode 35 can employ, for example, a multilayered structure of titanium (Ti) and titanium nitride (TiN). Since the lower electrode 35 is provided between the substrate 21 and the photoelectric conversion element 30, the lower electrode 35 serves as a light blocking layer, and can restrain light from entering the photoelectric conversion element 30 from the second principal surface S2 side of the substrate 21.

The photoelectric conversion element 30 is configured so as to include semiconductor layers having a photovoltaic effect. Specifically, the semiconductor layers of the photoelectric conversion element 30 include an i-type semiconductor layer 31, a p-type semiconductor layer 32, and an n-type semiconductor layer 33. The i-type semiconductor layer 31, the p-type semiconductor layer 32, and the n-type semiconductor layer 33 are formed of, for example, amorphous silicon (a-Si). The material of the semiconductor layers is not limited thereto, and may be, for example, polysilicon or microcrystalline silicon.

The a-Si of the p-type semiconductor layer 32 is doped with impurities to form a p+ region. The a-Si of the n-type semiconductor layer 33 is doped with impurities to form an n+ region. The i-type semiconductor layer 31 is, for example, a non-doped intrinsic semiconductor, and has lower conductivity than that of the p-type semiconductor layer 32 and the n-type semiconductor layer 33.

The i-type semiconductor layer 31 is provided between the n-type semiconductor layer 33 and the p-type semiconductor layer 32 in a direction orthogonal to a surface of the substrate 21 (in the third direction Dz). In the present embodiment, the n-type semiconductor layer 33, the i-type semiconductor layer 31, and the p-type semiconductor layer 32 are stacked on the lower electrode 35 in the order as listed.

With this configuration, the n-type semiconductor layer 33 of the photoelectric conversion element 30 is electrically coupled to the reset transistor Mrst and the source follower transistor Msf through the lower electrode 35 and the coupling wiring SLcn.

Upper electrode 34 is provided on the p-type semiconductor layer 32. The upper electrode 34 is formed of, for example, a light-transmitting conductive material such as indium tin oxide (ITO). The insulating film 27 is provided on the insulating film 26 so as to cover the photoelectric conversion element 30 and the upper electrode 34. The insulating film 27 is provided with the contact hole H1 in the region overlapping the upper electrode 34.

The coupling wiring 36 is provided on the insulating film 27, and is electrically coupled to the upper electrode 34 through the contact hole H1. The p-type semiconductor layer 32 is supplied with the reference potential VCOM (refer to FIG. 4) through the coupling wiring 36.

The photoelectric conversion element 30 is provided on the upper side of the insulating film 26, that is, on the upper side of the transistors and the capacitor Cad. In other words, the first and second electrodes 81 and 82 forming the capacitor Cad are hardly restricted by the arrangement and the shape of the photoelectric conversion element 30, and therefore, can be formed to have large areas using regions not overlapping the transistors. As a result, the capacitor Cad can have a large capacitance value.

The insulating film 28 is provided on the insulating film 27 so as to cover the upper electrode 34 and the coupling wiring 36. The insulating film 28 is provided as a protection layer for restraining water from entering the photoelectric conversion element 30. In addition, an insulating film 29 is provided on the insulating film 28 so as to cover the photoelectric conversion elements 30. The insulating film 29 is a hard coat film formed of an organic material. The insulating film 29 planarizes steps on a surface of the insulating film 28 formed by the photoelectric conversion elements 30 and the coupling wiring 36.

The cover member 122 is provided so as to cover the various transistors and the photoelectric conversion elements 30 with the adhesive layer 125 interposed therebetween. The adhesive layer 125 bonds the insulating film 29 to the cover member 122. The adhesive layer 125 is, for example, a light-transmitting optically clear adhesive (OCA) sheet.

Figure 9:
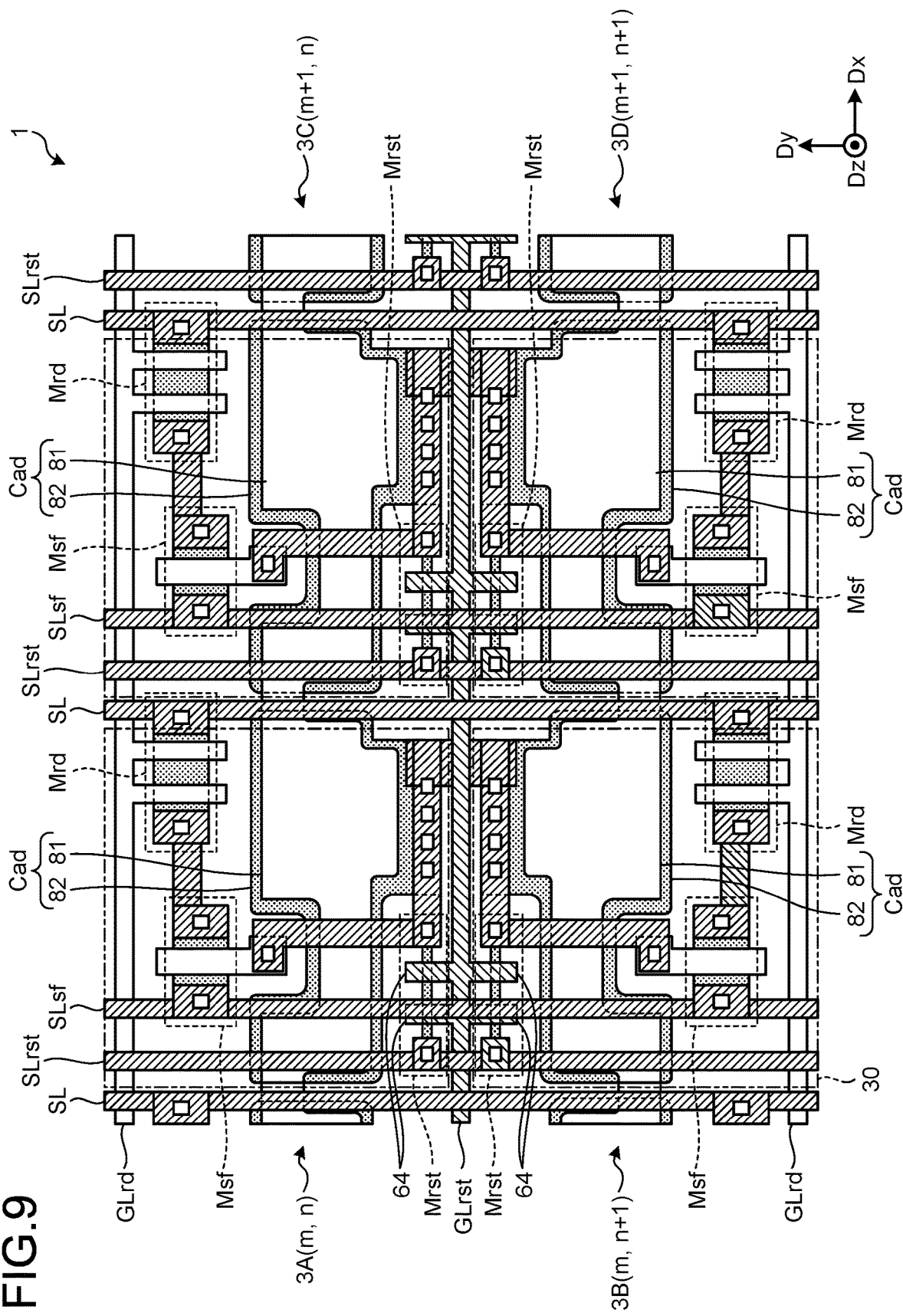
FIG. 9 is a plan view illustrating the detection elements.

FIG. 9 is a plan view illustrating the detection elements. For ease of viewing, FIG. 9 illustrates the photoelectric conversion elements 30 with long dashed double-short dashed lines. FIG. 9 illustrates four of the detection elements 3 in two rows and two columns. As illustrated in FIG. 9, a first detection element 3A is located at row m, column n (hereinafter, denoted as (m,n)); a second detection element 3B is located at (m,n+1); a third detection element 3C is located at (m+1,n); and a fourth detection element 3D is located at (m+1,n+1). The first detection element 3A and the second detection element 3B are provided adjacent to each other in the second direction Dy. The third detection element 3C is provided adjacent to the first detection element 3A in the first direction Dx. The fourth detection element 3D is adjacent to the third detection element 3C in the second direction Dy, and is adjacent to the second detection element 3B in the first direction Dx.

As described above, the reset control scan line GLrst is shared by the detection elements 3 adjacent in the second direction Dy. That is, the reset control scan line GLrst is provided between the first and second detection elements 3A and 3B, and is coupled to the first and second detection elements 3A and 3B. The reset control scan line GLrst is also provided between the third and fourth detection elements 3C and 3D, and is coupled to the third and fourth detection elements 3C and 3D.

Specifically, in the first and second detection elements 3A and 3B adjacent in the second direction Dy, the transistors, the first and second electrodes 81 and 82, and the various types of wiring are provided in a symmetric manner with respect to the reset control scan line GLrst using a virtual line parallel to the first direction Dx as an axis of symmetry. In the third and fourth detection elements 3C and 3D adjacent in the second direction Dy, the components are also provided in a symmetric manner with respect to the reset control scan line GLrst. In the first and third detection elements 3A and 3C adjacent in the first direction Dx, the transistors, the first and second electrodes 81 and 82, and the various types of wiring are provided in the same arrangement relation. The second and fourth detection elements 3B and 3D adjacent in the first direction Dx have the same arrangement relation.

The branches branching in the second direction Dy from the reset control scan line GLrst are provided in a symmetric manner with respect to the reset control scan line GLrst. The branches extending in one direction of the second direction Dy serve as the gate electrodes 64 of the reset transistor Mrst included in the first detection element 3A. The branches extending in the other direction of the second direction Dy serve as the gate electrodes 64 of the reset transistor Mrst included in the second detection element 3B.

With the above-described configuration, the common reset control signal RST is supplied from one of the reset control scan lines GLrst to the first and second detection elements 3A and 3B. In the same way, the common reset control signal RST is also supplied to the third and fourth detection elements 3C and 3D.

As described above, the detection device 1 of the present embodiment includes the substrate 21, the photoelectric conversion elements 30 arranged on the substrate 21, the transistors (the reset transistor Mrst, the source follower transistor Msf, and the read transistor Mrd) provided corresponding to each of the photoelectric conversion elements 30, and the scan lines (reset control scan lines GLrst) extending in the first direction Dx. Each of the detection elements 3 include the photoelectric conversion element 30 and the transistors provided so as to overlap the photoelectric conversion element 30. Each of the scan lines is provided between the first and second detection elements 3A and 3B adjacent in the second direction Dy intersecting the first direction Dx and is coupled to the first and second detection elements 3A and 3B.

In the detection device 1 of the present embodiment, the number of the reset control scan lines GLrst can be smaller than in a configuration in which the reset control scan line GLrst is provided for each of the detection elements 3 arranged in the second direction Dy. As a result, the arrangement pitch of the photoelectric conversion elements 30 in the second direction Dy can be reduced, whereby the sensor resolution of the detection device 1 can be improved.

As illustrated in FIG. 8, the photoelectric conversion element 30 is provided on the insulating film 26 and provided so as to overlap the transistors. As a result, the shape of the photoelectric conversion element 30 in the plan view is less restricted by the arrangement of the transistors, and has a high degree of freedom. That is, even in the configuration in which the transistors are provided so as to be symmetrical between the first and second detection elements 3A and 3B adjacent in the second direction Dy, the photoelectric conversion elements 30 can be arranged at a constant arrangement pitch in the second direction Dy.

Second Embodiment

Figure 10:
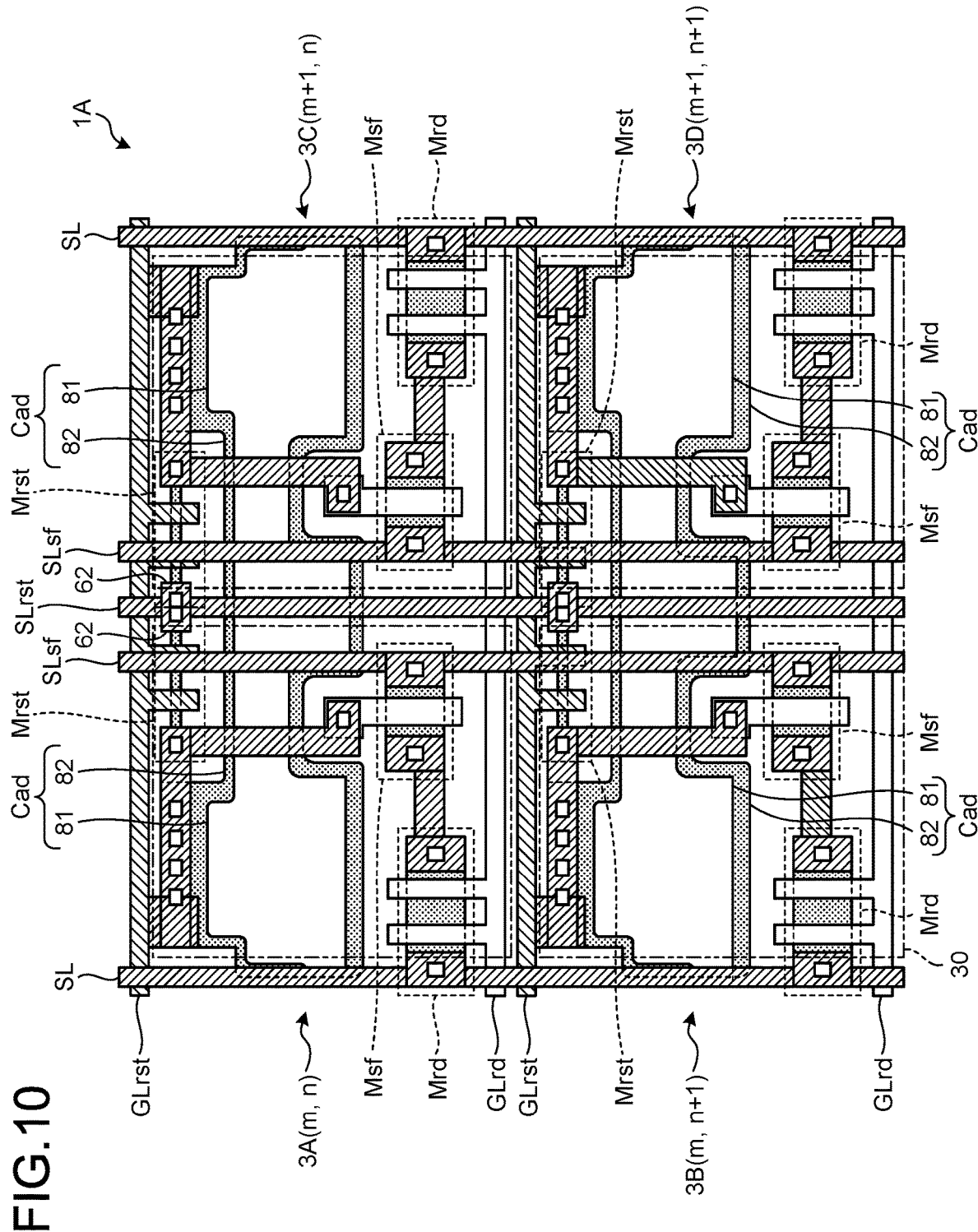
FIG. 10 is a plan view illustrating the detection elements according to a second embodiment of the present disclosure.

FIG. 10 is a plan view illustrating the detection elements according to a second embodiment of the present disclosure. In the following description, the same components as those described in the above-described embodiment are denoted by the same reference numerals, and will not be described again.

As illustrated in FIG. 10, in a detection device 1A of the second embodiment, the reset signal line SLrst is shared by the detection elements 3 adjacent in the first direction Dx. That is, the reset signal line SLrst is provided between the first and third detection elements 3A and 3C and is coupled to the first and third detection elements 3A and 3C. The reset signal line SLrst is also provided between the second and fourth detection elements 3B and 3D and is coupled to the second and fourth detection elements 3B and 3D.

Specifically, in the first and third detection elements 3A and 3C adjacent in the first direction Dx, the transistors, the first and second electrodes 81 and 82, and the various types of wiring are provided in a symmetric manner with respect to the reset signal line SLrst using a virtual line parallel to the second direction Dy as an axis of symmetry. In the first and second detection elements 3A and 3B adjacent in the second direction Dy, the transistors, the first and second electrodes 81 and 82, and the various types of wiring are provided in the same arrangement relation.

The signal lines are arranged in the first direction Dx in the order of the output signal line SL, the power supply signal line SLsf, the reset signal line SLrst, the power supply signal line SLsf, and the output signal line SL. The output signal line SL and the power supply signal line SLsf are provided in a symmetric manner with respect to the reset signal line SLrst.

The reset signal line SLrst is coupled to the semiconductor layer 61 of the reset transistor Mrst included in the first detection element 3A, and also coupled to the semiconductor layer 61 of the reset transistor Mrst included in the third detection element 3C. That is, the portion of the reset signal line SLrst coupled to the semiconductor layer 61 serves as the source electrode 62 of the reset transistor Mrst included in the first detection element 3A, and also serves as the source electrode 62 of the reset transistor Mrst included in the third detection element 3C.

With the above-described configuration, the reset potential Vrst is supplied from one of the reset signal lines SLrst to the first and third detection elements 3A and 3C. In the same way, the reset potential Vrst is also supplied to the second and fourth detection elements 3B and 3D.

In the detection device 1A of the present embodiment, the number of the reset signal lines SLrst can be smaller than in a configuration in which the reset signal line SLrst is provided for each of the detection elements 3 arranged in the first direction Dx. As a result, an arrangement pitch Px of the photoelectric conversion elements 30 in the first direction Dx can be reduced, whereby the sensor resolution of the detection device 1A can be improved.

Although the detection elements 3 adjacent in the first direction Dx share the reset signal line SLrst in the present embodiment, the present disclosure is not limited thereto. For example, the detection elements 3 adjacent in the first direction Dx may share the power supply signal line SLsf.

Third Embodiment

Figure 11:
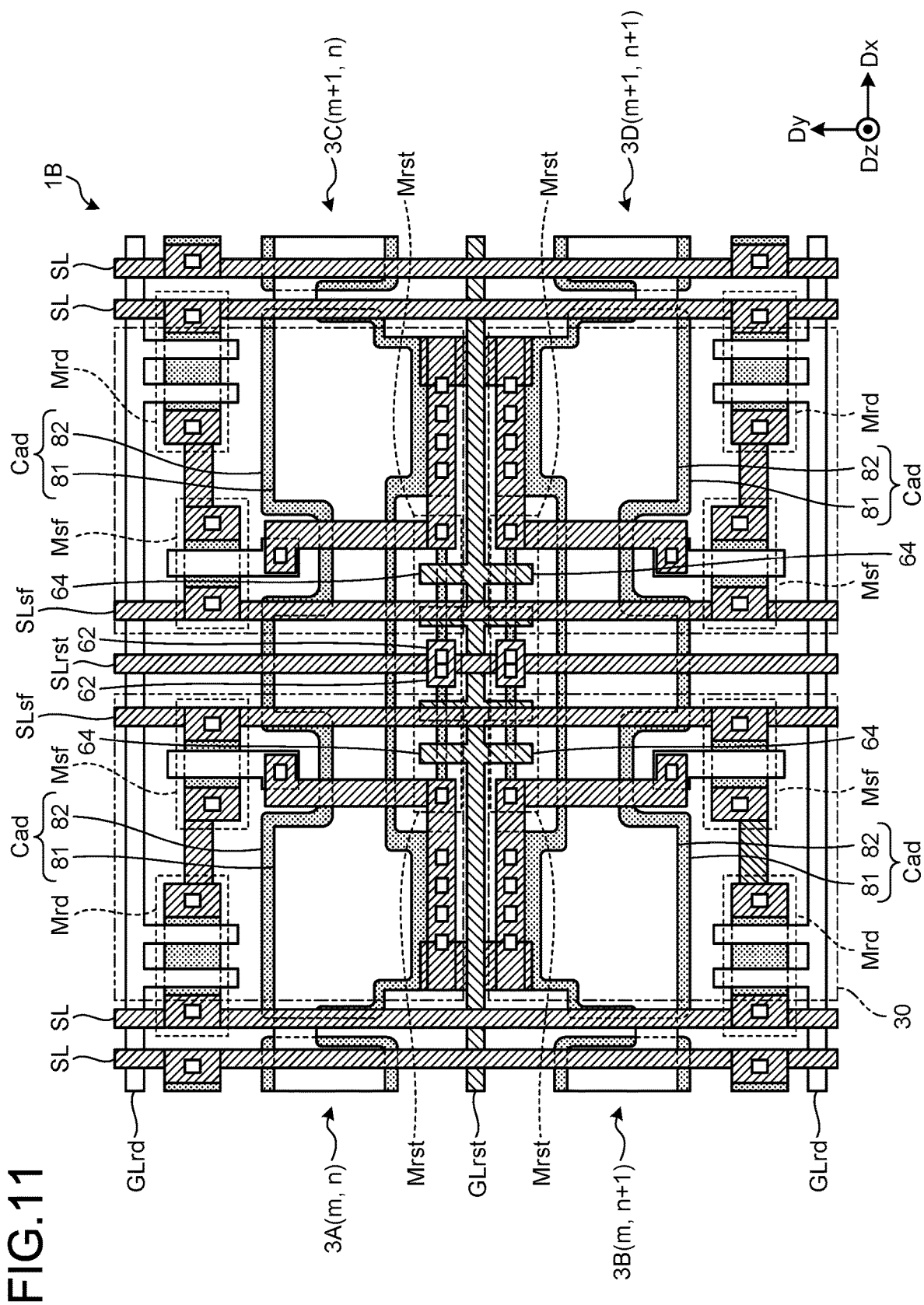
FIG. 11 is a plan view illustrating the detection elements according to a third embodiment of the present disclosure.

FIG. 11 is a plan view illustrating the detection elements according to a third embodiment of the present disclosure. As illustrated in FIG. 11, in a detection device 1B of the third embodiment, the reset control scan line GLrst is shared by the detection elements 3 adjacent in the second direction Dy, and the reset signal line SLrst is shared by the detection elements 3 adjacent in the first direction Dx.

That is, in the first and second detection elements 3A and 3B adjacent in the second direction Dy, the transistors, the first and second electrodes 81 and 82, and the various types of wiring are provided in a symmetric manner with respect to the reset control scan line GLrst using a virtual line parallel to the first direction Dx as an axis of symmetry. In addition, in the first and third detection elements 3A and 3C adjacent in the first direction Dx, the transistors, the first and second electrodes 81 and 82, and the various types of wiring are provided in a symmetric manner with respect to the reset signal line SLrst using a virtual line parallel to the second direction Dy as an axis of symmetry.

The coupling configuration of the reset control scan line GLrst to the first and second detection elements 3A and 3B adjacent in the second direction Dy is the same as that of the above-described first embodiment. The coupling configuration of the reset signal line SLrst to the first and third detection elements 3A and 3C adjacent in the first direction Dx is the same as that of the above-described second embodiment.

In the detection device 1B of the present embodiment, the arrangement pitch in the first direction Dx and the arrangement pitch in the second direction Dy of the photoelectric conversion elements 30 can be reduced, so that the detection device 1B can improve the sensor resolution.

While the preferred embodiments of the present disclosure have been described above, the present disclosure is not limited to the embodiments described above. The contents disclosed in the embodiments are merely exemplary, and can be variously changed within the scope not departing from the gist of the present disclosure. Any modification appropriately made within the scope not departing from the gist of the present disclosure also naturally belongs to the technical scope of the present disclosure.

What is claimed is:

1. A detection device comprising:
   a substrate;
   a plurality of photoelectric conversion elements provided to the substrate;
   a plurality of transistors provided corresponding to each of the photoelectric conversion elements; and
   a plurality of scan lines that extend in a first direction, wherein
   a plurality of detection elements each include
   a corresponding one of the photoelectric conversion elements and
   the transistors provided so as to overlap the corresponding one of the photoelectric conversion elements,
   the detection elements include a first detection element and a second detection element adjacent in a second direction intersecting the first direction,
   one of the scan lines is provided between the first detection element and the second detection element and is coupled to the first detection element and the second detection element,
   each of the detection elements includes a source follower transistor, a reset transistor, and a read transistor,
   the scan lines are reset control scan lines each configured to supply a reset control signal to the reset transistor,
   two of the reset transistors included in the first detection element and the second detection element adjacent in the second direction are electrically coupled to one of the reset control scan lines, and
   the read transistor of the first detection element and the read transistor of the second detection element are sequentially turned on in a continuous period in which the two of the reset transistors are on.

2. The detection device according to claim 1, wherein, in the first detection element and the second detection element adjacent in the second direction, the transistors included in the first detection element and the transistors included in the second detection element are provided in a symmetric manner with respect to the one of the scan lines.

3. The detection device according to claim 1, wherein the photoelectric conversion elements are arranged at a constant arrangement pitch in the second direction.

4. The detection device according to claim 1, further comprising:
   a plurality of signal lines that extend in the second direction and are configured to supply signals to the photoelectric conversion elements or any of the transistors; and
   a third detection element that is included in the detection elements and adjacent to the first detection element in the first direction, wherein
   one of the signal lines is provided between the first detection element and the third detection element adjacent in the first direction and is coupled to the first detection element and the third detection element.

5. The detection device according to claim 4, wherein, in the first detection element and the third detection element adjacent in the first direction, the transistors included in the first detection element and the transistors included in the third detection element are provided in a symmetric manner with respect to the one of the signal lines.

6. The detection device according to claim 4, wherein the photoelectric conversion elements are arranged at a constant arrangement pitch in the first direction.

7. The detection device according to claim 4, wherein
   the signal lines are reset signal lines each configured to supply a reset potential to the reset transistor, and
   two of the reset transistors included in the first detection element and the third detection element adjacent in the first direction are electrically coupled to one of the reset signal lines.

* * * * *